(12) United States Patent
Takano et al.

(10) Patent No.: US 9,074,987 B2
(45) Date of Patent: Jul. 7, 2015

(54) LUBRICANT DISTRIBUTION ACQUISITION DEVICE AND LUBRICANT DISTRIBUTION ACQUISITION METHOD

(75) Inventors: Takehisa Takano, Tokyo (JP); Hiroyuki Nose, Tokyo (JP); Akira Ito, Tokyo (JP)

(73) Assignee: IHI CORPORATION (JP)

( * ) Notice: Subject to any disclaimer, the term of this patent is extended or adjusted under 35 U.S.C. 154(b) by 0 days.

(21) Appl. No.: 14/002,788

(22) PCT Filed: Mar. 1, 2012

(86) PCT No.: PCT/JP2012/055220
§ 371 (c)(1),
(2), (4) Date: Sep. 3, 2013

(87) PCT Pub. No.: WO2012/121097
PCT Pub. Date: Sep. 13, 2012

(65) Prior Publication Data
US 2013/0341524 A1 Dec. 26, 2013

(30) Foreign Application Priority Data
Mar. 10, 2011 (JP) ................. 2011-053440

(51) Int. Cl.
| | | |
|---|---|---|
| G01N 23/05 | (2006.01) | |
| G01M 13/04 | (2006.01) | |
| F16C 19/06 | (2006.01) | |
| F16C 33/66 | (2006.01) | |
| F16C 19/52 | (2006.01) | |

(52) U.S. Cl.
CPC ............... *G01N 23/05* (2013.01); *F16C 19/06* (2013.01); *F16C 33/667* (2013.01); *F16C 19/52* (2013.01); *G01M 13/04* (2013.01)

(58) Field of Classification Search
CPC .............................. G01N 23/05; G01M 13/04
USPC ....................................................... 250/390.11
See application file for complete search history.

(56) References Cited

U.S. PATENT DOCUMENTS 4,152,598 A * 5/1979 Stewart ................ 250/391

FOREIGN PATENT DOCUMENTS

| JP | 07-260460 | 10/1995 |
|---|---|---|
| JP | 2000-292373 | 10/2000 |
| JP | 2000-292374 | 10/2000 |
| JP | 2005-195530 | 7/2005 |
| JP | 2007-101392 | 4/2007 |

(Continued)

OTHER PUBLICATIONS

"Nissan and Jaea Employ Nuclear Physics to Study Engine Lubrication—Precision high-speed neutron imaging system is world's first-", Nissan Motor Co., Ltd., Japan Atomic Energy Agency, No. 10, 2008.*
International Search Report mailed May 29, 2012 in corresponding PCT International Application No. PCT/JP2012/055220.
John T. Lindsay and Peter Schoch, "X-ray vision on steroids," Machine Design, vol. 70, No. 6, pp. 49-51, Apr. 1998.

(Continued)

*Primary Examiner* — Marcus Taningco
(74) *Attorney, Agent, or Firm* — Ostrolenk Faber LLP (57) ABSTRACT

The direction of the main axis of a bearing is adjusted by turning a supporting base (12a) that is supporting the bearing, and by then receiving a neutron beam that has been transmitted through the bearing from the direction of the main axis thereof, and converting it into an electromagnetic wave, and by then forming images using the received electromagnetic wave, lubricant distribution data that shows the distribution of a lubricant inside the bearing is acquired.

3 Claims, 5 Drawing Sheets

(56) References Cited

FOREIGN PATENT DOCUMENTS

| JP | 2010-054500 | 3/2010 |
| JP | 2010-286069 | 12/2010 |
| KR | 10-2009-0130617 | 12/2009 |

OTHER PUBLICATIONS

Korean Office Action, dated May 23, 2015, issued in corresponding Korean Patent Application No. 10-2013-7023575. English translation. Total 9 pages.

* cited by examiner

<ALIGNMENT IS GREATLY MISALIGNED>

FIG. 4B

<ALIGNMENT IS SOMEWHAT MISALIGNED>

FIG. 4C

<ALIGNMENT IS CORRECT>

FIG. 5

LUBRICANT DISTRIBUTION ACQUISITION DEVICE AND LUBRICANT DISTRIBUTION ACQUISITION METHOD

CROSS-REFERENCE TO RELATED APPLICATIONS

The present application is a 35 U.S.C. §§371 national phase conversion of PCT/JP2012/055220, filed Mar. 1, 2012, which claims priority to Japanese Patent Application No. 2011-053440, filed Mar. 10, 2011, the contents of which are incorporated herein by reference. The PCT International Application was published in the Japanese language.

FIELD OF THE INVENTION

The present invention relates to a lubricant distribution acquisition device and a lubricant distribution acquisition method.

BACKGROUND ART

For example, in Patent document 1, an invention is disclosed that uses neutron radiography to examine whether or not a lubricant is present inside a hydrodynamic bearing.

By using an invention disclosed in Patent document 1, without dismantling the bearing it has become possible to perform an examination to determine whether or not a lubricant is present which hitherto has required the bearing to be dismantled.

RELATED ART DOCUMENTS

Patent Documents

[Patent document 1] Japanese Patent Application, First Publication No. 2000-292373

DISCLOSURE OF THE INVENTION

Problems to be Solved by the Invention

In the invention disclosed in Patent document 1 it is possible to detect whether or not a lubricant is present. However, in the invention disclosed in Patent document 1, it is not possible to ascertain the way in which the lubricant is distributed over the entire inside of the bearing. As a consequence, it has not been possible to learn in detail the behavior of the lubricant.

One means of countering the above-described problems that may be considered is to convert a neutron beam that has been transmitted through a bearing from the direction of the main axis thereof into an electromagnetic wave and to then acquire images of this so as to acquire the distribution of a lubricant in a radial direction and the like around the main axis.

In order to accurately acquire the distribution of a lubricant it is necessary to accurately match the incident direction, which is the direction in which the neutron beam enters into the bearing, with the direction of the main axis of the bearing. However, it is quite possible that the direction of the main axis of the bearing may become mismatched with the incident direction because of vibration or the like generated in the device.

An aspect of the present invention was conceived in view of the above-described drawback, and it is an object thereof to provide a lubricant distribution acquisition device and a lubricant distribution acquisition method that make it possible to accurately match the direction of the main axis of a bearing with the incident direction of a neutron beam, and to thereby ascertain in detail the behavior of a lubricant inside a bearing.

The applicants for the present invention conducted research into the relationship between the behavior of a lubricant inside a bearing and the lifespan of the bearing. As a result, they discovered that individual differences existed between the lifespans of different bearings even when the environment and the like in which they were used were the same. Furthermore, they also dismantled and examined these bearings having different lifespans. As a result, they found that there were considerable differences in the state of the lubricant present inside the bearings. In a roller bearing, in particular, they found that the behavior of the lubricant inside the bearing had a huge effect on the lifespan.

These results suggest that the lifespan of a bearing depends on the behavior of the lubricant inside it. Namely, if the behavior of the lubricant inside a bearing can be ascertained, then there is a possibility that the lifespan of the bearing may be able to be improved.

Based on these research results, a first aspect of the present invention is a lubricant distribution acquisition device and employs a constitution in which there are provided: an alignment device that has a supporting base that supports a bearing, and that adjusts the direction of a main axis of the bearing by turning the supporting base; an electromagnetic wave converting device that receives a neutron beam that has been transmitted through the bearing from the direction of the main axis thereof, and converts it into an electromagnetic wave; and an imaging processing device that, by receiving the electromagnetic wave emitted from the electromagnetic wave converting device and using the electromagnetic wave to form an image, acquires lubricant distribution data that shows the distribution of a lubricant inside the bearing.

A second aspect of the present invention is the above-described first aspect of the present invention wherein a constitution is employed in which an alignment target whose projection shape changes when it is turned is able to be installed on the supporting base, and there is provided a control unit that controls the alignment device based on the shape of the alignment target which is contained in the imaging data acquired by the imaging processing device.

A third aspect of the present invention is the above-described second aspect of the present invention wherein a constitution is employed in which the alignment target is a rod-shaped component, and the control unit determines that the adjustment of the direction of the main axis being performed by the alignment device is complete when the shape of the alignment target which is contained in the imaging data reaches its smallest size.

A fourth aspect of the present invention is any one of the above-described first through third aspects of the present invention wherein a constitution is employed in which a bearing unit that is formed by combining a rotation drive device that drives the bearing to rotate, and the bearing into a single integrated unit can be removably attached to the supporting base.

A fifth aspect of the present invention is a lubricant distribution acquisition method and employs a constitution in which the direction of a main axis of a bearing is adjusted by turning a supporting base that is supporting the bearing, and by receiving a neutron beam that has been transmitted through the bearing from the direction of the main axis thereof, and converting it into an electromagnetic wave, and by forming images using the received electromagnetic wave, lubricant distribution data that shows the distribution of a lubricant inside the bearing is acquired.

Effects of the Invention

According to the present invention, by providing a supporting base that supports the bearing and by turning this supporting base, it is possible to adjust the direction of the main axis of the bearing.

Because of this, the direction of the main axis of the bearing can be made to constantly coincide with the incident direction of the neutron beam. Accordingly, according to the present invention, it is possible to accurately match the direction of the main axis of a bearing with the incident direction of a neutron beam.

Moreover, in the present invention, by changing a neutron beam that has been irradiated onto a bearing from the direction of the main axis of the bearing and has been transmitted through the bearing into an electromagnetic wave, and then forming an image from the received electromagnetic wave, lubricant distribution data that shows the distribution of lubricant inside the bearing is acquired.

Because of this, according to the present invention, it is possible to acquire lubricant distribution data that includes the distribution of a lubricant in a radial direction centered on the main axis without having to dismantle the bearing. As a result, it is possible to ascertain in detail the behavior of the lubricant inside the bearing.

As is described above, according to the present invention, it is possible to accurately match the direction of the main axis of a bearing with the incident direction of a neutron beam, and to thereby ascertain in detail the behavior of a lubricant inside a bearing.

EMBODIMENTS FOR CARRYING OUT THE INVENTION

Embodiments of the lubricant distribution acquisition device and lubricant distribution acquisition method of the present invention will now be described with reference made to the drawings. Note that in the following drawings, the scale of each component has been suitably altered in order to make each component a recognizable size.

First Embodiment

Figure 1A:
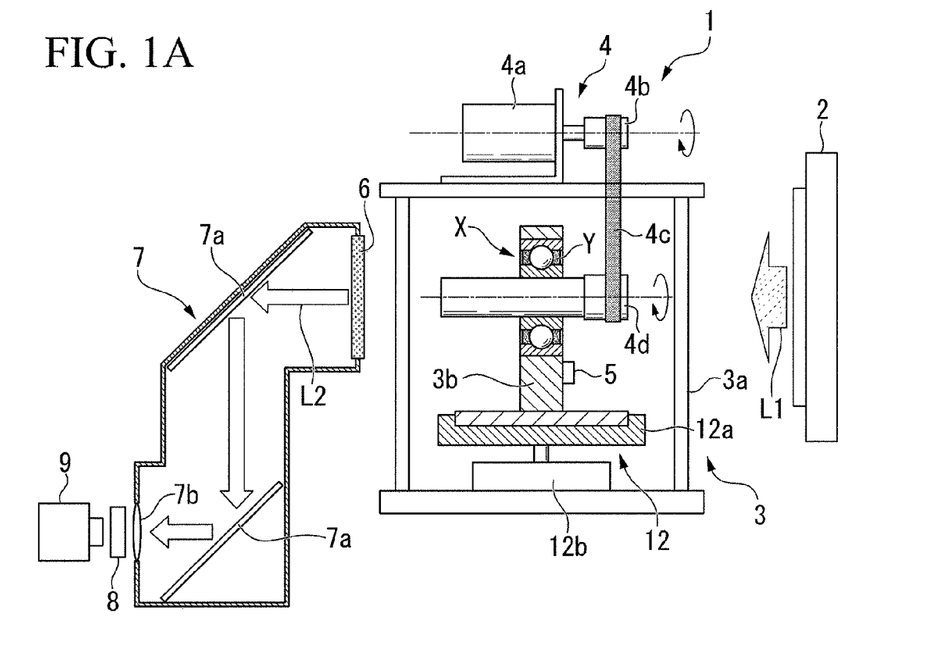
FIG. 1A shows in typical view the schematic structure of a lubricant distribution acquisition device according to a first embodiment of the present invention, and is a typical view of a portion of the mechanism thereof.
Figure 1B:
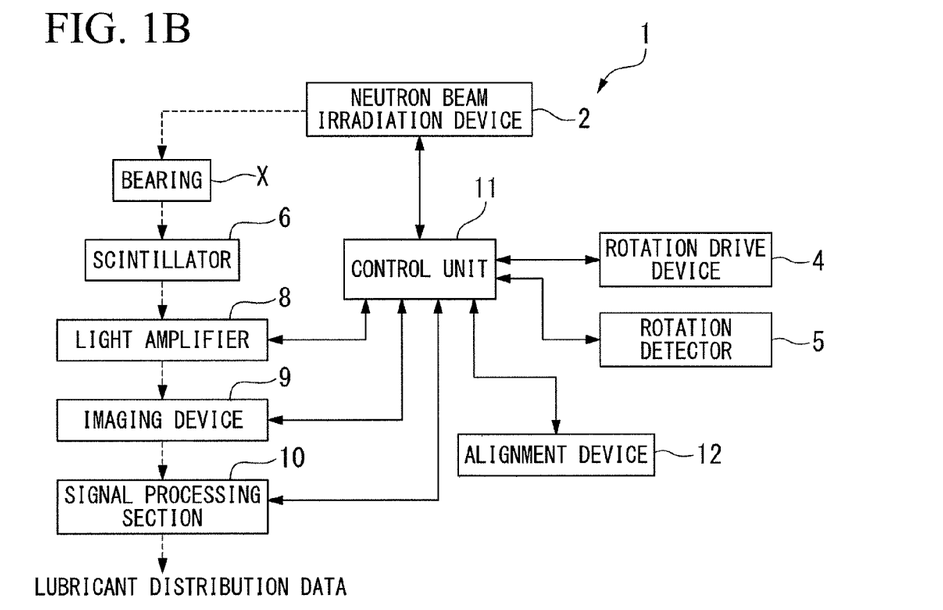
FIG. 1B shows in typical view the schematic structure of a lubricant distribution acquisition device according to the first embodiment of the present invention, and is a block diagram showing a portion of the functional structure thereof.

FIGS. 1A and 1B show in typical form the schematic structure of a lubricant distribution acquisition device 1 of the present embodiment. FIG. 1A is a typical view showing a portion of the mechanism of the lubricant distribution acquisition device 1. FIG. 1B is a block diagram showing a portion of the functional structure of the lubricant distribution acquisition device 1.

The lubricant distribution acquisition device 1 of the present embodiment ascertains the behavior of a lubricant Y (for example, grease) during the rotation of a bearing X, which is a ball bearing, by acquiring the distribution of the lubricant Y inside the bearing X.

In addition, as is shown in FIGS. 1A and 1B, the lubricant distribution acquisition device 1 of the present embodiment is provided with a neutron beam irradiation device 2, a bearing support mechanism 3, a rotation drive device 4 (i.e., a rotation drive means), a rotation detector 5, a scintillator 6 (i.e., an electromagnetic wave converting device), a light guide mechanism 7, a light amplifier 8, an imaging device 9, a signal processing section 10, a control unit 11 (i.e., a control means), and an alignment device 12 (i.e., an alignment means).

The neutron beam irradiation device 2 guides a neutron beam L1 emitted from a neutron source such as, for example, an atomic reactor so as to irradiate it onto the bearing X from the direction of the main axis of the bearing.

Note that if it is possible to irradiate the neutron beam emitted from the neutron source onto the bearing X from direction of the main axis of the bearing without having to guide the neutron beam, then it is also possible to omit the neutron beam irradiation device 2.

Moreover, in the lubricant distribution acquisition device 1 of the present embodiment, it is also possible to provide a separate neutron source that generates neutron beams by irradiating ions of hydrogen or helium or the like that have been generated by an ion generator, for example, onto a target.

The bearing support mechanism 3 supports the bearing X, and is provided with a case body 3a and a housing 3b.

The case body 3a is a frame body or box-shaped component that contains inside it the housing 3b and the bearing X that is fixed to the housing 3b. In the present embodiment, as is shown in FIG. 1A, the case body 3a also functions as a support base for the rotation drive device 4.

The housing 3b covers the outer ring of the bearing X, and supports the bearing X such that the bearing X can be removably connected thereto. In addition, in the present embodiment, as is shown in FIG. 1A, the housing 3b supports the bearing X such that the main axis of the bearing X faces towards the neutron beam irradiation device 2 side.

Note that it is preferable for the case body 3a and the housing 3b to be shaped such that they avoid the transmission area of the neutron beam L1, however, if they are formed from an aluminum material or the like that has an extremely low neutron beam L1 absorption rate, then the case body 3a and the housing 3b may be shaped such that they span across the transmission area of the neutron beam L1.

The rotation drive device drives the bearing X to rotate. As is shown in FIG. 1A, the rotation drive device 4 is provided with a motor 4a (i.e., a motive power unit) that generates motive power that is used to drive the bearing X to rotate, a pulley 4b that is used to transmit the motive power generated by the motor 4a to the bearing X by means of a belt, a belt 4c (i.e., a belt-shaped component), and a driveshaft portion 4d.

More specifically, the pulley 4b is joined by a coupling or the like to a shaft portion of the motor 4a. The driveshaft portion 4d is a rod-shaped component that is elongated in the direction of the main axis of the bearing X. The driveshaft portion 4d is fixed to the inner ring of the bearing X, and is placed horizontally so as to penetrate the center of the bearing X. The belt 4c is formed by an endless belt, and is entrained between the pulley 4b and the driveshaft portion 4d.

Note that marks or magnetic bodies that are used by the rotation detector 5 to detect the state of rotation of the driveshaft portion 4d are provided on the circumferential surface of the driveshaft portion 4d.

The rotation detector 5 detects the rotation of the inner ring of the bearing X (namely, detects the rotation of the bearing X) that is fixed to the driveshaft portion 4d by detecting the rotation of the driveshaft portion 4d.

The rotation detector 5 is formed by an optical detector or a magnetic detector that detects the marks or magnetic bodies that are provided on the circumferential surface of the driveshaft portion 4d and, as is shown in FIG. 1A, is fixed to the housing 3b.

The scintillator 6 receives the neutron beam L1 that has been transmitted through the bearing X and then emits light L2, and converts the neutron beam L1 into visible light.

For example, LiF/ZnS (Ag), BN/ZnS (Ag), $Gd_2O_3$/ZnS (Ag), $Gd_2O_3S$ (Tb) can be used for the scintillator 6.

The light guide mechanism 7 guides the light L2 emitted from the scintillator 6 to the imaging device 9 via the light amplifier 8.

As is shown in FIG. 1A, the light guide mechanism 7 is provided with a mirror 7a that reflects and guides the light L2, and with a lens 7b that condenses the light L2.

The light amplifier 8 raises the intensity of the light that enters into it via the light guide mechanism 7, and then outputs this light. For example, an image intensifier can be used for the light amplifier 8.

Note that if a sufficiently long exposure time can be guaranteed in the imaging device 9, then it is possible for the optical amplifier 8 to be omitted.

The imaging device 9 receives the light L2 that was emitted from the scintillator 6 and that arrived via the light guide mechanism 7 and the light amplifier 8; and then forms an image using this light. The imaging device 9 outputs the result of this imaging as imaging data.

Note that although a CCD camera, an SIT tube camera, or a high-speed camera or the like can be used for the imaging device 9, the movement of the lubricant Y inside the bearing X that is rotating at a high speed of, for example, approximately 6000 rpm is extremely fast. Therefore, it is preferable for a high-speed camera that is capable of obtaining images at an extremely high frame rate of approximately 2000 fps to be used.

The signal processing section 10 processes imaging data input from the imaging device 9, and outputs it as requested lubricant distribution data.

The lubricant distribution data in the present embodiment is data that includes information pertaining to the distribution of a lubricant in a radial direction centered on the main axis, and information pertaining to the thickness distribution of the lubricant in the direction of the main axis. The signal processing section 10 of the present embodiment, for example, calculates lubricant distribution data from the brightness information in the imaging data, and performs processing to associate this lubricant distribution data with the detection results from the rotation detector 5.

Note that the information pertaining to the distribution of a lubricant in a radial direction centered on the main axis, and the information pertaining to the thickness distribution of the lubricant in direction of the main axis are contained in the actual imaging data itself that was obtained by the imaging device 9. Therefore, it is also possible for requested lubricant distribution data to be in the form of imaging data. In this case, the signal processing section 10 outputs the imaging data input from the imaging device 9 as lubricant distribution data without modifying it in any way.

Note that in the present embodiment, the imaging processing device of the present invention is formed by the imaging device 9 and the signal processing section 10.

The control unit 11 controls the overall operations of the lubricant distribution acquisition device 1 of the present embodiment. As is shown in FIG. 1B, the control unit 11 is electrically connected to the neutron beam irradiation device 2, the rotation drive device 4, the rotation detector 5, the light amplifier 8, the imaging device 9, the signal processing section 10, and the alignment device 12.

The alignment device 12 performs alignments such that direction of the main axis of the bearing X matches the incident direction of the neutron beam L1. As is shown in FIG. 1A, the alignment device 12 is provided with a supporting base 12a and a turning device 12b.

The supporting base 12a is formed such that the aforementioned housing 3b which supports the bearing X is able to engage with it, and is indirectly contact with the bearing X as it supports it.

The turning device 12b turns the supporting base 12a within a horizontal plane and, under the control of the control unit 11, sets the turn angle of the supporting base 12a.

The direction of the main axis of the bearing can be adjusted by the alignment device 12 causing the supporting base 12a to turn.

Note that as a result of the housing 3b engaging with the supporting base 12a, the positional relationship between the main axis of the bearing X that is fixed to the housing 3b and the supporting base 12a is unmistakably determined.

Accordingly, even if the housing 3b and the bearing X are not installed on the supporting base 12a, by adjusting the turn angle the direction of the main axis of the bearing X can be adjusted.

Moreover, in the lubricant distribution acquisition device 1 of the present embodiment, the direction of the main axis of the bearing can also be adjusted when the housing 3b and the bearing X are not installed on the supporting base 12a (this is described below in detail).

Figure 2:
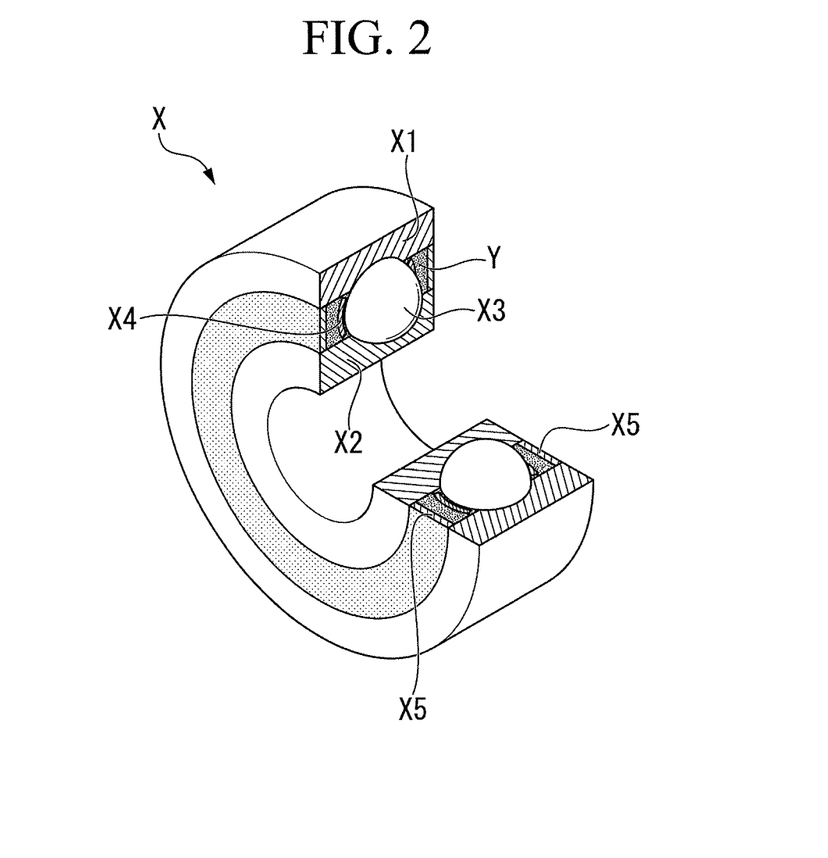
FIG. 2 is a perspective view of a cutaway model showing the schematic structure of a bearing that is installed in the lubricant distribution acquisition device according to the first embodiment of the present invention.

The bearing X is a ball bearing (i.e., a roller bearing) that contains a lubricant inside it and, in the present embodiment, is formed as a radial bearing.

FIG. 2 is a perspective view of a cutaway model showing the schematic structure of the bearing X. As is shown in FIG. 2, the bearing X is provided with a toroidal outer ring X1 and a toroidal inner ring X2 that are positioned opposite each other in a radial direction, a plurality of balls X3 that are located between the outer ring X1 and the inner ring X2, a holder X4 that is used to maintain equidistant intervals between adjacent balls X3, and seals X5 that seal off the spaces where the balls X3 are housed.

Note that in order to raise the visibility of the lubricant Y in the imaging data and to thereby acquire a more accurate distribution, it is desirable that component elements of the bearing X do not appear in the imaging data. Because of this, it is preferable for these component elements of the bearing X (i.e., the outer ring X1, the inner ring X2, the balls X3, the holder X4, and the seals X5) to be formed from an aluminum material that has a low absorption rate of the neutron beam L1.

Next, operations (i.e., a lubricant distribution acquisition method) of the lubricant distribution acquisition device 1 of the present embodiment which is has the above-described structure will be described. Note that the main agent of the operations of the lubricant distribution acquisition device 1 of the present embodiment that are described below is the control unit 11.

Firstly, the control unit 11 causes the alignment device 12 to adjust the direction of the main axis of the bearing.

In this adjustment of the direction of the main axis of the bearing, in the present embodiment, an alignment jig 100 (shown in FIGS. 3A and 3B) that is able to be engaged with the supporting base 12a is used.

Figure 3A:
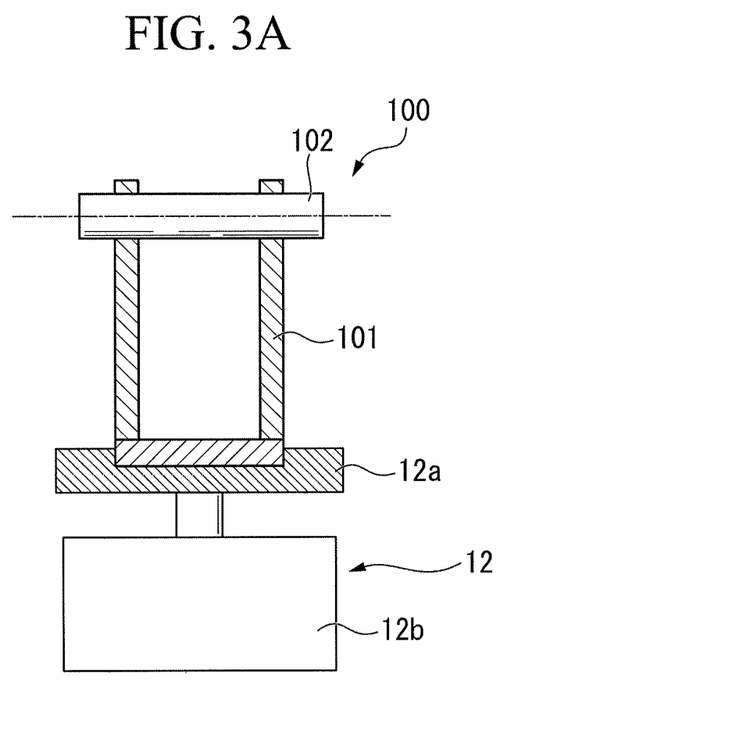
FIG. 3A is a schematic structural view of an alignment jig used in the lubricant distribution acquisition device according to the first embodiment of the present invention.
Figure 3B:
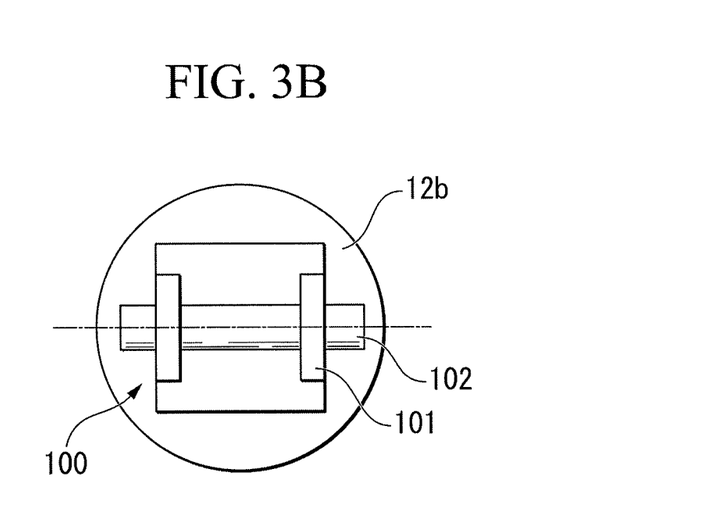
FIG. 3B is a schematic structural view of an alignment jig used in the lubricant distribution acquisition device according to the first embodiment of the present invention.

The alignment jig 100 is provided with a supporting portion 101 and an alignment target 102.

The supporting portion 101 supports the alignment target 102, and is set in a shape that enables it to engage with the supporting base 12a.

The alignment target 102 is a circular columnar rod-shaped component whose projection shape is changed as it is turned. The alignment target 102 is supported by the supporting portion 101 such that, when the supporting portion 101 is engaged with the supporting base 12a, the axial direction (i.e., the longitudinal direction) of the alignment target 102 matches the direction of the main axis of the bearing. The alignment target 102 is formed from a material that has a high rate of neutron beam absorption, and has sufficient rigidity to prevent its shape being deformed.

As is described above, in the lubricant distribution acquisition device 1 of the present embodiment, the alignment target 102 is constructed such that it is able to be installed on the supporting base 12a.

In addition, when the alignment target 102 has been installed on the supporting base 12a, the control unit 11 causes the imaging device 9 to acquire images at the same time as it causes the alignment device 12 to turn the supporting base 12a.

There are cases when the axial direction of the alignment target 102 is considerably out of alignment with the incident direction of the neutron beam L1 (namely, cases when the main axis of the bearing is considerably out of alignment with the incident direction of the neutron beam L1). In such cases, as is shown in FIG. 4A, a projection shape R of the alignment target 102 in the imaging data is considerably stretched in the left-right direction.

Figure 4A:
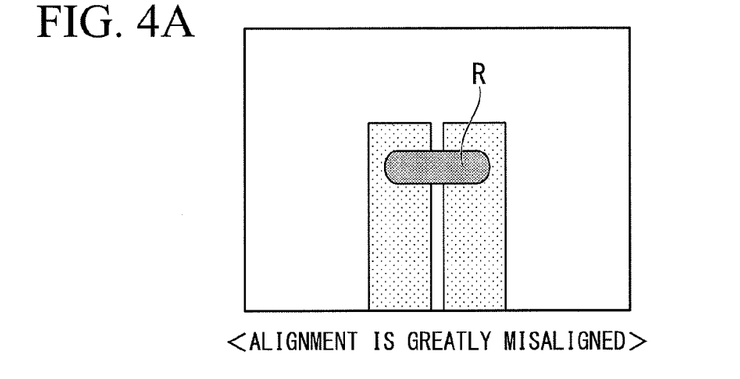
FIG. 4A is an explanatory view that is used to describe an axial direction adjustment in the lubricant distribution acquisition device according to the first embodiment of the present invention.
Figure 4B:
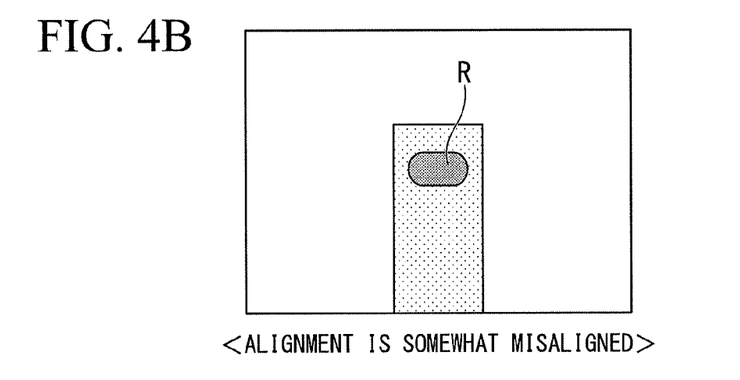
FIG. 4B is an explanatory view that is used to describe an axial direction adjustment in the lubricant distribution acquisition device according to the first embodiment of the present invention.

When the supporting base 12a is turned so that the axial direction of the alignment target 102 approaches the incident direction of the neutron beam L1, then as is shown in FIG. 4B, the projection shape R of the alignment target 102 in the imaging data becomes smaller than how it appears in FIG. 4A.

Figure 4C:
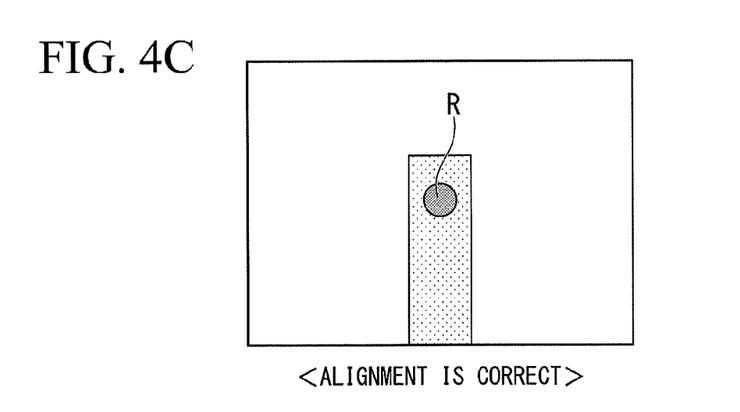
FIG. 4C is an explanatory view that is used to describe an axial direction adjustment in the lubricant distribution acquisition device according to the first embodiment of the present invention.

When the axial direction of the alignment target 102 coincides with the incident direction of the neutron beam L1 (i.e., when the main axis of the bearing matches the incident direction of the neutron beam L1), then as is shown in FIG. 4C, the projection shape R of the alignment target 102 in the imaging data reaches its smallest size.

In the lubricant distribution acquisition device 1 of the present embodiment, the state when the projection shape R of the alignment target 102 is the smallest is stored in advance in the control unit 11. When the projection shape R of the alignment target 102 that is contained in the imaging data reaches its smallest size, the control unit 11 determines that the adjustment of the direction of the main axis of the bearing by the alignment device 12 is complete, and stops the alignment device 12.

When the adjustment of the direction of the main axis of the bearing by the alignment device 12 is complete, the alignment jig 100 is removed from the supporting base 12a, and the housing 3b that holds the bearing X is installed on the supporting base 12a.

As is described above, the direction of the main axis of the bearing X and the axial direction of the alignment target 102 are set such that they coincide. Because of this, the direction of the main axis of the bearing X that has been installed on the supporting base 12a also coincides with the incident direction of the neutron beam L1.

According to the lubricant distribution acquisition device 1 and the lubricant distribution acquisition method of the present embodiment, it is possible to make the direction of the main axis of the bearing X accurately match the incident direction of the neutron beam L1.

Next, after the rotation drive device 4 has been connected to the bearing X, the control unit 11 causes the rotation drive device 4 to rotate the bearing X. As a result of this, the inner ring X2 of the bearing X is driven to rotate, and the balls X3 that are sandwiched between the inner ring X2 and the outer ring X1 revolve around the main axis at the same time as they are rotated around their own axis. As a consequence, the lubricant Y moves through the interior of the bearing X in conjunction with the movement of the balls X3.

Next, the neutron beam L1 is guided by the neutron beam irradiation device 2 and, as is shown in FIG. 1A, when the neutron beam L1 enters into the bearing X from the direction of the main axis of the bearing X, the neutron beam L1 that has been transmitted through the bearing X then enters into the scintillator 6.

When the neutron beam L1 enters into the scintillator 6, the scintillator 6 emits light L2 that has the same intensity distribution as the intensity distribution of the neutron beam L1. Namely, the scintillator 6 converts the neutron beam L1 into the light L2 and then emits this light L2.

The light L2 emitted from the scintillator 6 is guided by the light guide mechanism 7 and amplified by the light amplifier 8, and then enters into the imaging device 9.

The control unit 11 then causes the imaging device 9 to create an image. As a result of this, imaging data is acquired by the imaging device 9.

Next, the control unit 11 causes the signal processing section 10 to process the imaging data. According to this, the control unit 11 causes lubricant distribution data that includes information pertaining to the distribution of the lubricant in a radial direction centered on the main axis, and information pertaining to the thickness distribution of the lubricant in the direction of the main axis to be calculated.

The control unit 11 also performs processing to associate the calculated lubricant distribution data with the detection results from the rotation detector 5. As a result of this, the lubricant distribution data is output in association with the rotation angle of the bearing X.

The lubricant Y is formed from an organic material and has a higher rate of neutron beam absorption than does the bearing X. Because of this, the neutron beam L1 that has been transmitted through the bearing X is greatly attenuated in areas where the lubricant Y is present. In contrast, the intensity distribution of neutron beam L1 is proportional to the intensity distribution of the light L2 into which the neutron beam L1 has been converted.

Accordingly, the neutron beam L1 is irradiated onto the bearing X from the direction of the main axis thereof, and then images of the light L2 into which the neutron beam L1 that is transmitted through the bearing X has been converted are acquired. By doing this, it is possible to acquire from the brightness distribution of the image data the distribution of the lubricant Y in a radial direction centered on the main axis.

Moreover, the amount of attenuation of the neutron beam L1 is proportional to the thickness of the lubricant Y in areas through which the neutron beam L1 is transmitted. Namely, the greater the thickness of the lubricant Y in these transmission areas, the greater the amount of attenuation of the neutron beam L1, and the intensity of the neutron beam L1 after being transmitted through these areas is reduced. In contrast, the intensity distribution of the neutron beam L1 is proportional to the intensity distribution of the light L2 into which the neutron beam L1 is converted. Accordingly, the neutron beam L1 is irradiated onto the bearing X from the direction of the main axis thereof, and images of the light L2 into which the neutron beam L1 that is transmitted through the bearing X has been converted are acquired. According to this, it is possible to acquire from the brightness distribution of the image data the thickness distribution of the lubricant in the direction of the main axis thereof.

In addition, in the lubricant distribution acquisition device 1 and the lubricant distribution acquisition method of the present embodiment, the neutron beam L1 that has been irradiated onto the bearing X from the direction of the main axis thereof and has been transmitted through the bearing X is changed into the light L2, and then images are formed from the received light L2. As a result, lubricant distribution data that shows the distribution of the lubricant Y inside the bearing X is acquired.

Because of this, according to the lubricant distribution acquisition device 1 and the lubricant distribution acquisition method of the present embodiment, it is possible to acquire lubricant distribution data that includes the distribution of the lubricant Y in a radial direction centered on the main axis and also includes the thickness distribution of the lubricant Y in direction of the main axis without having to dismantle the bearing X. As a result, it is possible to ascertain in detail the behavior of the lubricant Y inside the bearing X.

Second Embodiment

Next, a second embodiment of the present invention will be described. Note that in the description of the second embodiment, any description of portions thereof that are the same as those of the first embodiment is either omitted or simplified.

Figure 5:
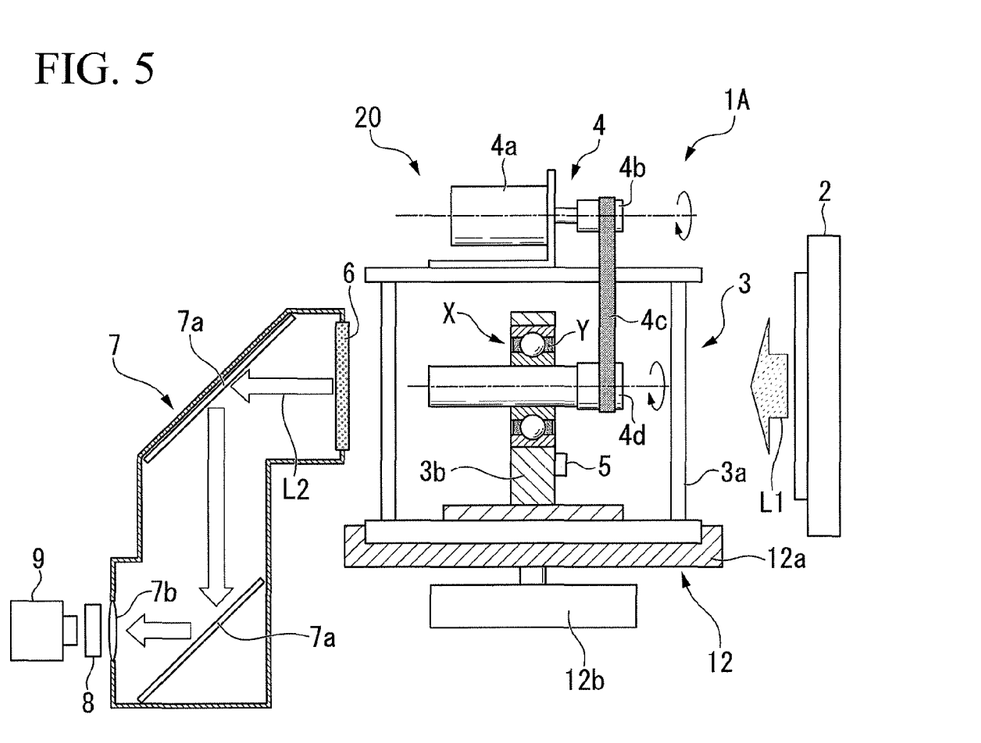
FIG. 5 is a typical view showing a portion of the structure of a lubricant distribution acquisition device according to a second embodiment of the present invention.

FIG. 5 is a typical view showing a portion of the mechanism of a lubricant distribution acquisition device 1A of the present embodiment. As is shown in FIG. 5, in the lubricant distribution acquisition device 1A of the present embodiment, a bearing unit 20 that is formed by combining the bearing support mechanism 3, the rotation drive device 4, and the bearing X into a single integrated unit can be removably attached to the supporting base 12a.

According to the lubricant distribution acquisition device 1A of the present embodiment, if a plurality of the bearing units 20 are prepared then it is possible to acquire lubricant distribution data over a prolonged period of time by replacing the bearing units 20.

At this time, the rotation drive device 4 is contained within the beating unit 20. Because of this, it is possible to prevent the rotation drive device 4 from becoming radioactive due to a prolonged exposure to neutron beams.

Moreover, in the lubricant distribution acquisition device 1A of the present embodiment, it is possible to accurately match the direction of the main axis of the bearing with the incident direction of the neutron beam L1 by means of the alignment device 12. Because of this, even if the bearing unit 20 is replaced, the direction of the main axis can be made to continuously and accurately match the incident direction of the neutron beam L1.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

For example, in the above-described embodiment, a structure is described in which the direction of the main axis of the bearing is adjusted using the alignment target 102.

However, the present invention is not limited to this, and it is also possible, for example, to adjust the direction of the main axis using the actual bearing X itself from imaging data obtained by acquiring images of the bearing X.

However, the alignment target 102 is specially designed for aligning the direction of the main axis of the bearing. Because of this, by using the alignment target 102, as in the above-described embodiments, a suitable shape for adjusting the direction of the main axis can be employed. As a result, the direction of the main axis can be adjusted more accurately.

Note that the shape of the alignment target is not limited to being a rod shape, and it is only necessary for the projection shape thereof to change as a result of the alignment target being turned.

Moreover, in the rotation drive device it is also possible to use a toothed pulley together with a toothed belt. It is also possible for a sprocket (i.e., a wheel portion) and a chain (i.e., a belt-shaped component) to be used.

Moreover, in the above-described embodiments, a structure in which the bearing X is a ball bearing that receives a load in a radial direction is described.

However, it is also possible for the present invention to be used to ascertain the behavior of a lubricant inside other types of bearing such as, for example, roller bearings, sliding bearings, and bearings that receive a load in a thrust direction.

Moreover, in the above-described embodiments, a structure in which the neutron beam L1 is converted into light L2 using the scintillator 6 is described.

However, the present invention is not limited to this and it is also possible to acquire images by converting the neutron beam L1 into radioactive rays (i.e., electromagnetic waves) such as gamma rays and the like.

Moreover, in the above-described embodiments, a structure in which digital photography is performed by the imaging device 9 is described.

However, the present invention is not limited to this and it is also possible for film photography to be performed by the imaging device.

INDUSTRIAL APPLICABILITY

According to the present invention, by providing a supporting base that supports a bearing and by turning this supporting base, it is possible for the direction of the main axis of the bearing to be adjusted. Because of this, the direction of the main axis of the bearing can be made to constantly coincide with the incident direction of the neutron beam. Accordingly, according to the present invention, it is possible to accurately match the direction of the main axis of a bearing with the incident direction of a neutron beam.

DESCRIPTION OF THE REFERENCE NUMERALS 1, 1A . . . Lubricant distribution acquisition device,
2 . . . Neutron beam irradiation device,
4 . . . Rotation drive device,
5 . . . Rotation detector,
6 . . . Scintillator (Electromagnetic wave converting means),
8 . . . Light amplifier,
9 . . . Imaging device,
10 . . . Signal processing section,
11 . . . Control unit (Control means),
12 . . . Alignment device (Alignment means),
12a . . . Supporting base,
12b . . . Turning device,
20 . . . Bearing unit,
L1 . . . Neutron beam,
L2 . . . Light (Electromagnetic waves),
X . . . Bearing,
Y . . . Lubricant,
102 . . . Alignment target

The invention claimed is:

1. A lubricant distribution acquisition device comprising:
an alignment device that has a supporting base that supports a bearing, and that adjusts the direction of a main axis of the bearing by turning the supporting base;
an electromagnetic wave converting device that receives a neutron beam that has been transmitted through the bearing from the direction of the main axis thereof, and converts it into an electromagnetic wave; and
an imaging processing device that, by receiving the electromagnetic wave emitted from the electromagnetic wave converting device and using the electromagnetic wave to form an image, acquires lubricant distribution data that shows the distribution of a lubricant inside the bearing,
wherein an alignment target whose projection shape changes when it is turned is able to be installed on the supporting base;
there is provided a control unit that controls the alignment device based on the shape of the alignment target which is contained in the imaging data acquired by the imaging processing device;
the alignment target is a rod-shaped component; and
the control unit determines that the adjustment of the direction of the main axis being performed by the alignment device is complete when the shape of the alignment target which is contained in the imaging data reaches its smallest size.

2. The lubricant distribution acquisition device according to claim 1, wherein a bearing unit that is formed by combining a rotation drive device that drives the bearing to rotate, and the bearing into a single integrated unit can be removably attached to the supporting base.

3. A lubricant distribution acquisition method comprising:
an adjustment step of adjusting the direction of a main axis of a bearing by turning a supporting base that supports the bearing; and
an acquisition step of acquiring lubricant distribution data that shows the distribution of a lubricant inside the bearing by receiving a neutron beam that has been transmitted through the bearing from the direction of the main axis thereof, and converting the neutron beam into an electromagnetic wave, and forming images using the received electromagnetic wave, wherein:
in the adjustment step, an alignment target, whose projection shape changes when the alignment target is turned, is installed on the supporting base, and the direction of the main axis is adjusted based on the shape of the alignment target, which is contained in imaging data acquired by receiving the neutron beam that has been transmitted through the alignment target, and converting the neutron beam into the electromagnetic wave, and forming images using the received electromagnetic wave;
the alignment target is a rod-shaped component; and
in the adjustment step, the adjustment of the direction of the main axis is determined to be complete when the shape of the alignment target which is contained in the imaging data reaches its smallest size.

* * * * *